US012753847B2

(12) United States Patent
Gunin et al.

(10) Patent No.: US 12,753,847 B2
(45) Date of Patent: Oct. 6, 2026

(54) SYSTEM OF VALVES FOR CELL CULTURE MACHINE

(71) Applicant: CELLAVEN, Breteniere (FR)

(72) Inventors: Suriya Gunin, Boisseuilh (FR); Julien Maruotti, Auribeau-sur-Siagne (FR)

(73) Assignee: CELLAVEN (SAS), Bretenieres (FR)

( * ) Notice: Subject to any disclaimer, the term of this patent is extended or adjusted under 35 U.S.C. 154(b) by 35 days.

(21) Appl. No.: 18/862,289

(22) PCT Filed: May 2, 2023

(86) PCT No.: PCT/EP2023/061550
§ 371 (c)(1),
(2) Date: Nov. 1, 2024

(87) PCT Pub. No.: WO2023/213811
PCT Pub. Date: Nov. 9, 2023

(65) Prior Publication Data

US 2025/0290570 A1 Sep. 18, 2025

(30) Foreign Application Priority Data

May 3, 2022 (FR) ...................................... 2204195

(51) Int. Cl.
*F16K 11/16* (2006.01)
*A61M 39/28* (2006.01)
(Continued)

(52) U.S. Cl.
CPC ........... *F16K 11/163* (2013.01); *C12M 29/00* (2013.01); *C12M 41/44* (2013.01); *F16K 7/063* (2013.01);
(Continued)

(58) Field of Classification Search
CPC combination set(s) only.
See application file for complete search history.

(56) References Cited

U.S. PATENT DOCUMENTS 5,056,992 A * 10/1991 Simons ................ F04B 43/021 417/474
5,273,517 A * 12/1993 Barone ............ A61M 1/36226 417/474
(Continued)

FOREIGN PATENT DOCUMENTS

JP H0691010 A * 4/1994 ....... B29C 66/73921
JP H09303582 A 11/1997
(Continued)

OTHER PUBLICATIONS

International Search Report issued on Aug. 2, 2023, in corresponding International Application No. PCT/EP2023/061550, 4 pages.

*Primary Examiner* — Binh Q Tran
(74) *Attorney, Agent, or Firm* — Maier & Maier, PLLC

(57) ABSTRACT

A device for controlling the passage of a liquid into a series of flexible tubes, including a set of clamps, each being able to clamp a flexible tube, and a first jaw arranged on a lever and a second jaw forming a pincer with said first jaw, each lever being pivotably mounted between an open position in which the clamp is open and a closed position in which said clamp is closed, and a set of wheels mounted for conjoint rotation about the same axis A, each of the wheels forming a cam and being associated with one of said levers, and the rotation of each wheel enables the passage of said lever from its closed position to its open position, and vice versa.

14 Claims, 2 Drawing Sheets

(51) Int. Cl.

| | |
|---|---|
| ***C12M 1/00*** | (2006.01) |
| ***C12M 1/34*** | (2006.01) |
| ***F16K 3/18*** | (2006.01) |
| ***F16K 7/06*** | (2006.01) |
| ***F16K 11/078*** | (2006.01) |
| ***F16K 31/05*** | (2006.01) |
| ***F16K 31/52*** | (2006.01) |
| ***F16K 31/60*** | (2006.01) |

(52) U.S. Cl.

CPC ............ *A61M 39/284* (2013.01); *F16K 3/184* (2013.01); *F16K 7/065* (2013.01); *F16K 11/0785* (2013.01); *F16K 31/055* (2013.01); *F16K 31/52* (2013.01); *F16K 31/602* (2013.01)

(56) References Cited

U.S. PATENT DOCUMENTS

| | | | | |
|---|---|---|---|---|
| 2005/0053501 | A1* | 3/2005 | Akahori ............ | F16K 31/52491 417/474 |
| 2010/0211002 | A1* | 8/2010 | Davis ................ | A61M 5/14228 604/67 |
| 2017/0354941 | A1* | 12/2017 | Brown .................... | B01F 25/31 |
| 2023/0272863 | A1* | 8/2023 | Gloor ...................... | F16K 7/045 137/636.1 |

FOREIGN PATENT DOCUMENTS

| | | | |
|---|---|---|---|
| WO | 2014038024 | A1 | 3/2014 |
| WO | 2017070503 | A2 | 4/2017 |

* cited by examiner

[Fig 1]
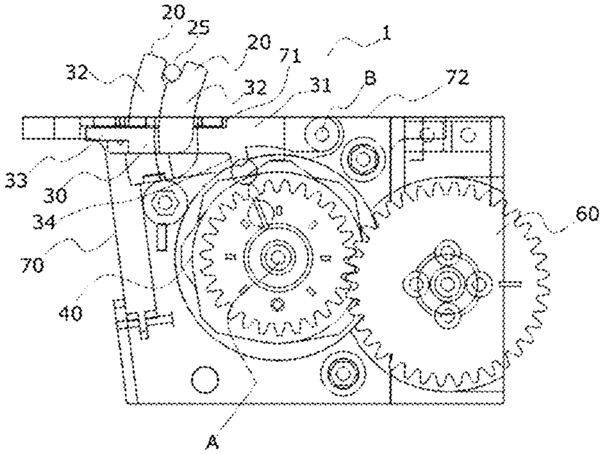
[Fig 2]
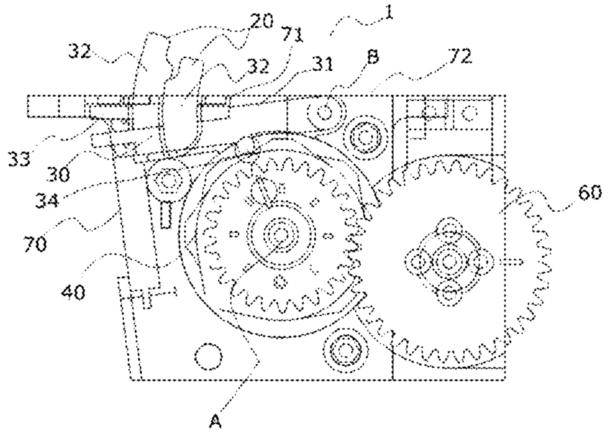
[Fig 3]
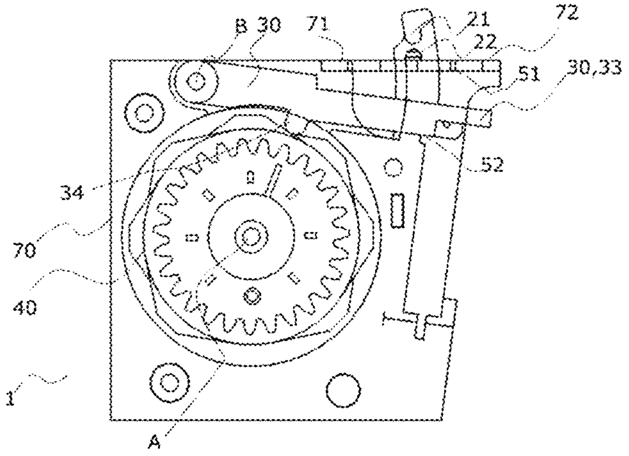

[Fig 4]
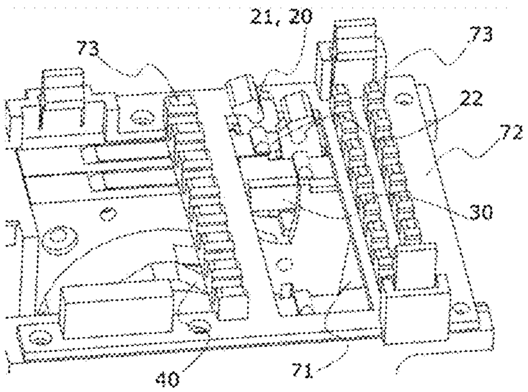

SYSTEM OF VALVES FOR CELL CULTURE MACHINE

TECHNICAL FIELD

The present invention relates to the field of scientific equipment. More particularly, the present invention relates to the field of control of fluid circulation. More particularly, the device according to the invention is intended for managing the distribution of a culture medium in cell culture dishes.

BACKGROUND

The cell culture is an essential element of research in biology. In particular, it is used for studying cell behaviour and the production of recombinant proteins or viruses. To this end, the adherent or suspended cells are cultured in a liquid medium inside gas and temperature regulated enclosures.

Apart from industrial production devices, cell culture requires numerous human manipulations. The cells are cultured in dishes placed in a dedicated oven. To feed the cells and evacuate the produced wastes, an operator should regularly renew the culture medium by drawing the spent medium and reintroducing fresh medium. In addition, the cell density should be monitored. An excessively low or excessively high density prevents the homogeneous growth thereof. Consequently, the operator should regularly draw cells in large amounts to discard them or distribute them in other culture dishes. All these manipulations consume a lot of time (including weekends and holidays) and equipment (e.g. pipettes). Moreover, the regular opening and closure of the culture dishes and of the bottles containing the culture medium are major sources of bacterial contaminations.

Hence, there is an important need to eliminate as much as possible human interventions in the process of cell culture in vitro.

Automated devices are already available on the market. Nonetheless, the installation thereof costs several hundreds of thousands of euros and they require numerous dedicated consumables. These devices are suitable for industrial production but not on the scale of the research and development laboratory.

Ideally, a cell culture machine should be able to adapt to the equipment already existing inside the laboratory. Thus, it should be compact and light in order to fit in ovens next to culture dishes. Alternatively, the machine should be able to be placed next to the oven. Advantageously, it is modular in order to be able to adapt to different configurations.

Among the central modules of a cell culture machine, mention may be made of the pump(s) which feed the medium to the culture dishes as well as the valves which will control the passage of the liquid towards the dishes and/or towards the draining or cell collection recipients.

To facilitate cleaning and avoid contamination, the valves should not be in direct contact with the culture medium. This last constraint excludes the use of rotary valves.

Moreover, the valves should be light, compact, easy to manufacture and energy-efficient. Hence, considering the use of a pinch solenoid valve in this field is unlikely.

Hence, there is still a need for a valve system, suited for a cell culture machine complying with the previously-described constraints.

SUMMARY

Thus, the present invention relates to a device for controlling the passage of a liquid into a series of flexible tubes, comprising:

a set of clamps, each being able to clamp a flexible tube, and comprising a first jaw arranged on a lever and a second jaw forming a pincer with said first jaw, each lever being pivotably mounted between an open position in which said clamp is open and a closed position in which said clamp is closed, and a set of wheels mounted for conjoint rotation about the same axis A, each of said wheels forming a cam and being associated with one of said levers, characterised in that the rotation of each wheel enables the passage of said lever from its closed position to its open position, and vice versa.

According to a preferred embodiment of the invention, said device comprises a first stop limiting movement of said lever in the open position and a second stop limiting movement in the closed position.

In the context of the present invention, by the expression “able to clamp a tube”, it should be understood the fact that said clamp is able to clamp at least one tube. In a preferred embodiment of the invention, said clamp is able to clamp one single tube or two tubes. Embodiments wherein more than two tubes could be arranged between each clamp may also be considered.

According to a preferred embodiment of the invention, each lever is biased in the closed position via an elastic means.

According to a preferred embodiment of the invention, the elastic means is a spring.

According to a preferred embodiment of the invention, said second jaw is fixed.

According to a preferred embodiment of the invention, said first and second jaws of two contiguous clamps are arranged in a staggered manner.

According to a preferred embodiment of the invention, each second stop is arranged so that said first and second jaws are not in contact in the closed position.

According to a preferred embodiment of the invention, said first and second jaws are separated by a space equivalent to that of the thickness of a flexible tube when it is crushed.

According to a preferred embodiment of the invention, each second stop is arranged such that each lever does not bear on the cam track when said lever is in the closed position.

According to a preferred embodiment of the invention, each lever comprises an arm which extends perpendicularly to the axis of rotation A.

According to a preferred embodiment of the invention, each lever is pivotably mounted about an axis B parallel to the axis of rotation A.

According to a preferred embodiment of the invention, each lever comprises an arm from which an L-like shaped blade (tab) extends perpendicularly.

According to a preferred embodiment of the invention, each lever comprises, at its distal end, a tab intended to enable opening of the clamp by a user.

According to a preferred embodiment of the invention, each wheel comprises two parallel planar faces delimiting a cam profile comprising a neutral area, an ascending area, a constant level area and a descending area.

According to a preferred embodiment of the invention, said set of wheels is associated with a motor with determination of the angular position (60) capable of driving said set of wheels in rotation about the axis A.

BRIEF DESCRIPTION OF THE FIGURES

FIG. 1 shows a profile view of an embodiment of a device according to the invention.

FIG. 2 shows a profile view of an embodiment of a device according to the invention.

FIG. 3 shows a profile view of an embodiment of a device according to the invention.

FIG. 4 shows a top view of an embodiment of a device according to the invention.

DETAILED DESCRIPTION

The device 1 comprises a set of clamps 20, each being able to clamp a flexible tube 25 in which a culture medium flows, and comprising a first jaw 21 arranged on a lever 30 and a second jaw 22 forming a pincer with said first jaw 21. Each lever 30 is pivotably mounted between an open position in which said clamp 20 is open, in which the culture medium can flow, and a closed position in which said clamp 20 is closed and the culture medium can no longer flow.

The change in position of each of the clamps 20 is controlled by a wheel 40 belonging to a set of wheels 40 mounted for conjoint rotation about the same axis A, each of said wheels 40 forming cam is associated with one of said levers 30.

In particular, the device 1 according to the invention is intended to be arranged between the culture medium source and the culture dishes and/or the collection dishes and recipients. Alternative configurations may be considered. In some embodiments, it is possible to connect the medium sources to a buffer recipient in which the source media are mixed. In the last embodiment, the device 1 according to the invention, arranged between the medium sources and said buffer recipient, allows accurately metering the amount of each of the source media.

The embodiment described hereinafter comprises two devices 1 according to the invention, a first one arranged between the culture medium source and the culture dishes and a second one arranged between the culture dishes and a recipient for collecting the spent media or cells. Other embodiments may be considered by using two head-to-tail devices 1 arranged between the culture medium sources and the culture dishes allowing routing K medium sources towards N dishes. Similarly, two head-to-tail devices 1 may be arranged between the culture dishes and the recipients for collecting the spent media or cells, allowing routing N culture dishes towards J recipients for collecting the spent media or cells.

The culture medium may be arranged in chambers each connected to a first tube intended to channel the culture medium from said enclosure.

The embodiment described hereinafter comprises one single source of culture medium. Nonetheless, it is quite possible to consider using several sources of culture medium to be able to increase the amount of available medium or to be able to use several different culture media intended, alone or as a mixture, for a particular cell type.

Said first tube communicates with a series of flexible tubes intended to feed the culture medium to the culture dishes.

The connection between said first tube and said series of flexible tubes may be ensured via an intermediate part comprising an inlet, intended to be connected to said first tube, and a series of outlets each intended to be connected to one of the flexible tubes of the series of flexible tubes.

Said intermediate part may be in the form of a part comprising, between its inlet and its series of outlets, a set of channels connecting said inlet to each of the outlets such that the liquid originating from said inlet is distributed between each of the outlets.

In particular, said intermediate part may be obtained by moulding or additive printing. Preferably, it is made of plastic. In the last case, it should be understood that said intermediate part may be manufactured at a limited cost and thus form a consumable that could be replaced after each use cycle.

The circulation of the culture medium from its source towards the cell culture dishes may be generated by a pump placed at any point of the circuit.

In order to evacuate the used culture medium from the culture dishes towards a recipient for collecting the spent media or cells, another device 1 according to the invention may be arranged between said recipient for collecting the spent media or cells and the culture dishes. Alternatively, the same device 1 as that one implemented between the source of culture medium and the culture dishes may be used to this end.

In a manner similar to what has been described before for the circulation of the culture medium from its source towards the culture dishes, the spent medium is drawn from each of the dishes via a flexible tube included in a series of flexible tubes. The latter may be connected to an intermediate part as described before comprising a series of inlets all communicating with the same outlet connected to the recipient for collecting the spent media or cells.

The circulation of the culture medium from the cell culture dishes towards the recipient for collecting the spent media or cells may be generated by a pump placed downstream of said dish. Said pump may be identical to or different from that one used for the circulation of the culture medium from its source towards the cell culture dishes.

The device 1 according to the invention will allow opening or closing the passage of the liquid in each flexible tube included in the series of flexible tubes. Said closure is caused by crushing of said flexible tube between two jaws 21, 22 of the same clamp 20.

The clamps 20, of the set of clamps 20, comprise:

a first jaw 21 arranged on a lever 30 and, a second jaw 22 forming a pincer with said first jaw 21.

The two jaws 21, 22 may have various shapes. Preferably, each of the two jaws 21, 22 has, in cross-section, a dome-like shape whose tip extends in the direction of the complementary jaw of the same pincer.

The lever 30 has a distal end and a proximal end between which an arm 31 extends. The proximal end comprises a compartment able to receive a rod forming a pivot axis B. Advantageously, the latter has a longitudinal axis perpendicular to the axis of the arm 31.

Advantageously, the distal end may comprise a tab 33 intended to enable opening of the clamp by a user. Said tab 33 enables the user to disengage the clamp 20 in the open position to place between the jaws 21, 22 one of the flexible tubes of the series of flexible tubes.

The first jaw 21 may be arranged at the surface of the arm 31. Alternatively, it may be offset vertically above or below said arm 31. In the last embodiment, the offset of the jaw 21 may be ensured via a blade 32 extending from the arm 31. Advantageously, the arm has an L-like shape on the base of which the first jaw 21 is placed.

The lever 30 further comprises a follower part 34 intended to interact with the cam profile. Advantageously, the follower part 34 is a stud extending from the arm 31 in the direction of the cam profile.

Preferably, the lever 30 is made in one-piece. Said lever arm 30 may be manufactured by moulding or by additive printing.

The second jaw 22 of the clamp 20 may be fixed or movable. Preferably, said jaw 22 is fixed. By "fixed", it should be understood the fact that, during the passage of the pincer from the open position to the closed position, the second jaw 22 is stationary, the pincer being closed only by bringing the first one 21 towards the second jaw 22. In the last embodiment, the second jaw 22 is advantageously arranged on the pathway intended to receive the flexible tube.

Advantageously, the movement of the jaws 21, 22 between said open position and said closed position may be limited by a first stop 51 limiting the movement of said lever in the open position and a second stop 52 limiting the movement in the closed position. Advantageously, the stops 51, 52 are arranged so as to limit the movement of the lever 30 and are even more advantageously associated with the frame 70.

Preferably, the stop 51 is arranged so that the space between the jaws 21, 22 is, when the lever 30 is in contact with said stop 51, larger than the thickness of a flexible tube at rest. The presence of said stop 51 allows avoiding the operator opening the pincer too wide and damaging the elastic means.

Preferably, the space between the jaws 21, 22 is, in the open position when the open position is caused only by the wheel 40, comprised between 95 and 99.9% of the thickness of a flexible tube at rest. Thus, in the open position, the flexible tube is held by friction between the two jaws 21, 22 of the pincer and cannot escape from the device 1 according to the invention. By "at rest", it should be understood the state of said tube, under normal temperature and pressure conditions, in the absence of specific pressure at its surface.

Preferably, the second stop 52 is arranged so that said first and second jaws 21, 22 are not in contact in the closed position. Thus, it should be understood that the presence of the stop 52 allows limiting the pressure exerted by the two jaws on the flexible tube in the closed position and the risks of wear, or rupture, of the flexible tube at the contact area with the jaws 21, 22. Even more advantageously, the stop is arranged so that said first and second jaws 21, 22 are separated by a space smaller than that of the thickness of a flexible tube when it is crushed and preferably comprised between 50 and 95% of the thickness of a flexible tube when it is crushed. By "thickness of a flexible tube when it is crushed", it should be understood a thickness substantially equivalent to the thickness of a wall of the flexible tube multiplied by two. Thus, the maximum crushing of the flexible tube enables the creation of a sealed area preventing the passage of a fluid without damaging the flexible tube.

By default, each lever 30 is advantageously biased in the closed position via an elastic means. The latter will apply a force on the lever 30 which is thus held in contact with the stop 52. Preferably, a first end of said elastic means is associated with the frame 70 containing the device 1 according to the invention whereas the other end is associated with the levier 30. Said elastic means may take on all forms known to a person skilled in the art like for example leaf springs and coil springs.

Advantageously, the wheel 40 forming cam comprises two parallel planar faces delimiting a cam profile. Preferably, the latter is decomposed into several successive areas. A first area, so-called the "neutral" area, in which the cam profile does not modify the position of the lever 30 held in the closed position under the effect of the elastic means. According to a less preferred embodiment, in the absence of said elastic means, the "neutral" area could induce the passage and holding of the lever 30 in the closed position. Next, the cam profile comprises a second area, so-called the "ascending" area, in which the cam profile interacts, by direct or indirect bearing, on the lever 30 to make it pass from its closed position to its open position. A third area, so-called the "constant level" area, during which the cam profile interacts, by direct or indirect bearing, on the lever 30 to hold it in the open position. A fourth area, so-called the "descending" area in which the cam profile interacts, by direct or indirect bearing, on the lever 30 to make it pass from its open position to its closed position. Said ascending area is arranged upstream of the neutral area so as to obtain a cycle where these four areas succeed one another indefinitely by rotation of the wheel 40 forming cam. In particular, said cam profile may be obtained by using an ovoid cam profile with a flat top. The latter corresponds to said constant level area.

Advantageously, the profile of the descending and ascending areas is adjusted to offer the lowest resistance to the levers and thus reduce the torque of the motor used for the rotation of the wheels 40 forming cams. This enables the device 1 according to the invention to use motors of smaller sizes and weights and lower consumption.

The cam profile and its different areas are adapted to the position of the stops 51, 52. A person skilled in the art is capable of determining the most suitable cam profile that will enable the passage of the lever 30 from its closed position to its position open without having to force on the stops 51, 52.

The constant level is deliberately flat, offering a locally stable position of the follower part 34 of the lever 30, allowing cutting off the power supply of the motor most of the time, without any risk of slippage of the wheel.

Preferably, the stop 52, the cam profile and/or the follower part 34 are arranged such that the follower part 34 is not in direct contact with the cam profile when the lever 30 is in the closed position. This last embodiment has the advantage of limiting frictions of the follower part 34 on the cam profile and thus limiting wear of these two parts and the amount of energy required for the rotation of the wheel 40.

To ensure the compactness of the device 1 according to the invention, the lateral bulk of each pincer is advantageously equivalent to 110% to 120% of that of a crushed flexible tube when said pincers are in the closed position. In the case where said pincer is intended to receive more than one flexible tube, the lateral bulk of said pincer is adapted accordingly.

Preferably, the flexible tubes used in the context of the present invention have a thickness comprised between 0.5 mm and 10 mm.

Preferably, the clamps 20 of a set of clamps 20 will be arranged parallel to one another. More particularly, the longitudinal axes of each lever 30 of a set of clamps 20 will be parallel to one another.

Even more preferably, the clamps 20 of the same set of clamps 20 are arranged side-by-side, separated from one another by a space required to avoid frictions between said clamps 20 during closure of their pincer.

Preferably, all of the second jaws 22 of the same set of clamps 20 are arranged at the surface of the same plane. In order to facilitate the set-up of the flexible tubes between the pincers of two contiguous clamps, it is advantageous to alternatively arrange the second jaws 22, of the same set of clamps 20, on two lines spaced apart by at least the width of a flexible tube. Thus, said first and second jaws 21, 22 of two contiguous clamps 20 are arranged in a staggered manner. In the embodiment where the offset of the jaw 21 is ensured via a blade 32 extending from the arm 31, the fact that said first and second jaws 21, 22 of two contiguous clamps 20 are arranged in a staggered manner means that the two blades 32 of two contiguous clamps are alternately arranged on two lines spaced apart by at least the width of a flexible tube.

Preferably, in order to facilitate the set-up of the flexible tubes, the lever 30 or the distal end of the lever 30 is pivotably mounted relative to the rest of the device 1 such that the first one 21 could be cleared away from the second jaw 22. In doing so, access to the outer surface 72 is improved.

Preferably, the wheels 40 of the set of wheels 40 have identical size and shape. Said wheels 40 are mounted for conjoint rotation about the same axis A. By "conjoint", it should be understood the fact that all wheels 40 of the same set of wheels 40 rotate simultaneously about the axis a.

According to an even more preferred embodiment, the wheels 40 of the same set of wheels 40 are arranged so that the portion of the cam profile comprising the ascending, constant level and descending (corresponding to the opening phase of the pincers) areas is offset from one wheel to another. Even more preferably, said portion occupies a different angular position for each wheel 40 of the set of wheels 40. Thus, it should be understood that an angular position of the set of wheels 40 corresponds to opening of one single pincer of the set of clamps 20.

Preferably, the set of wheels 40 is associated with a motor 60 able to drive said set of wheels 40 in rotation about the axis A. Even more preferably, a motor with determination of the angular position 60 and quite preferably a servomotor. The constant knowledge of the angular position of the motor 60 allows automatically deducing the position of the set of wheels 40 and consequently the position of each of the pincers of the set of clamps 20.

The association between the motor 60 and the set of wheels 40 may be achieved by any means known to a person skilled in the art. Among these, mention may in particular be made of gears, belts and direct coupling on the shaft of the set of wheels 40.

Advantageously, the device 1 according to the invention comprises a frame 70 on which the motor 60, the set of wheels 40 and the set of clamps 20 will be fastened.

Preferably, said frame forms an enclosure with a substantially parallelepiped shape.

Preferably, the motor 60 and the set of wheels 40 are arranged inside the frame 70.

Even more preferably, the set of clamps 20 is partially arranged inside the frame 70.

Quite preferably, said frame 70 comprises an opening 71 enabling access to the jaws 21, 22 of each of the clamps of the set of clamps 20. Advantageously, said jaws 21, 22 are arranged outside the frame 70.

This last embodiment enables the user to easily access the pincers to place the flexible tubes therein without having to open the frame 70.

Preferably, the frame 70 may comprise an outer surface 72 on either side of the opening 71 enabling access to the jaws 21, 22. Advantageously, this surface may receive guides 73 intended to block each of the flexible tubes on either side of its respective pincer.

The present invention also relates to a cell culture machine characterised in that it comprises at least one device 1 according to the invention.

In addition to the device 1 according to the invention, the cell culture machine according to the invention may comprise an electronic system controlling in particular the rotation of the motor 60 according to the invention. Moreover, said electronic system may also control the operation of the pump when the latter is integrated into the cell culture machine according to the invention.

A mode of use is described hereinafter. The user places in a temperature and gas controlled oven, a number n of culture dishes, a device 1 according to the invention under the control of an electronic system, a bottle containing culture medium, a recipient intended to collect the spent media or cells.

A first tube is arranged between the culture medium bottle and the inlet of a disposable intermediate part. The outlets of the intermediate part are connected to N flexible tubes each connected at their other end to each of the N culture dishes.

Each flexible tube is arranged between the guides 73 and then passed between the pincers of a clamp 20. To do so, the user acts on the tab 33 to move the lever 30 and open the pincer. Alternatively, the user could program the sequential opening of the pincers via the electronic system. Once the flexible tube is in place, the pincer returns back to the closed position under the effect of the elastic means. Thus, the flexible tube is closed and the passage of the culture medium is blocked.

The same operation is performed to connect the culture dishes to the enclosure intended to collect the wastes.

The electronic system comprises software which manages the rotation of the set of wheels 40 about its axis of rotation A. Each time it is necessary to add or draw from the medium inside a culture dish, the electronic system will actuate the motor 60 so that the latter drives the set of wheels 40 in rotation. The rotation is done until the wheel 40, triggering the lever 30 of the clamp 20 associated with the flexible tube, is positioned so that the portion of the cam profile triggering the opening of the clamp 20 interacts with the follower part 34. Once the follower part is opposite the constant level area, the rotation of the set of wheels 40 is stopped for the period necessary for the addition of culture medium. The passage of the culture medium is triggered by the activation of a pump by the electronic system.

Thus, feeding of the different culture dishes is carried out successively by rotation of the set of wheels 40. A complete rotation of this set of wheels 40 enables the successive opening of all clamps 20 and therefore feeding of all culture dishes. The same applies to the extraction of the spent medium.

The invention claimed is:

1. A device for controlling the passage of a liquid into a series of flexible tubes, comprising:

a set of clamps, each being able to clamp a flexible tube, and comprising a first jaw arranged on a lever and a second jaw forming a pincer with said first jaw, each lever being pivotably mounted between an open position in which said clamp is open and a closed position in which said clamp is closed, and a set of wheels mounted for conjoint rotation about the same axis A, each of said wheels forming a cam and being associated with one of said levers, the rotation of each wheel enables the passage of said lever from its closed position to its open position, and vice versa, and a first stop limiting movement of said lever in the open position and a second stop limiting movement in the closed position, and wherein position of the first jaw and the second jaw controls the passage of the liquid into the flexible tube.

2. The device for controlling the passage of a liquid into a series of flexible tubes according to claim 1, wherein each lever is biased in the closed position via an elastic means.

3. The device for controlling the passage of a liquid into a series of flexible tubes according to claim 2, wherein said elastic means is a spring.

4. The device for controlling the passage of a liquid into a series of flexible tubes according to claim 1, wherein said second jaw is fixed.

5. The device for controlling the passage of a liquid into a series of flexible tubes according to claim 1, wherein said first and second jaws of two contiguous clamps are arranged in a staggered manner.

6. The device for controlling the passage of a liquid into a series of flexible tubes according to claim 1, wherein each second stop is arranged so that said first and second jaws are not in contact in the closed position.

7. The device for controlling the passage of a liquid into a series of flexible tubes according to claim 1, wherein said first and second jaws are separated by a space equivalent to that of the thickness of a flexible tube when it is crushed.

8. The device for controlling the passage of a liquid into a series of flexible tubes according to claim 1, wherein each second stop is arranged such that each lever does not bear on the cam track when said lever is in the closed position.

9. The device for controlling the passage of a liquid into a series of flexible tubes according to claim 1, wherein each lever comprises an arm which extends perpendicularly to the axis of rotation A.

10. The device for controlling the passage of a liquid into a series of flexible tubes according to claim 1, wherein each lever is pivotably mounted about an axis B parallel to the axis of rotation A.

11. The device for controlling the passage of a liquid into a series of flexible tubes according to claim 1, wherein each lever comprises an arm from which an L-like shaped blade (tab) extends perpendicularly.

12. The device for controlling the passage of a liquid into a series of flexible tubes according to claim 1, wherein each lever comprises, at its distal end, a tab intended to enable opening of the clamp by a user.

13. The device for controlling the passage of a liquid into a series of flexible tubes according to claim 1, wherein each wheel comprises two parallel planar faces delimiting a cam profile comprising a neutral area, an ascending area, a constant level area and a descending area.

14. The device for controlling the passage of a liquid into a series of flexible tubes according to claim 1, wherein said set of wheels is associated with a motor with determination of the angular position capable of driving said set of wheels in rotation about the axis A.

* * * * *